United States Patent
Han et al.

(10) Patent No.: US 9,861,117 B2
(45) Date of Patent: Jan. 9, 2018

(54) ANIMAL FEED ADDITIVE AND ANIMAL FEED COMPRISING ALKYL ESTERS OF MEDIUM CHAIN FATTY ACIDS, AND THEIR USE IN ANIMAL FEED

(75) Inventors: Yanming Han, Nijmegen (NL); Coenraad Henricus Maria Smits, Malden (NL); John Brennan, Guelph (CA); Gregory Ian Page, Paris (CA); Johannes Teunis Pieter Van Dam, Veenendaal (NL)

(73) Assignee: Nutreco Nederland B.V., Boxmeer (NL)

( * ) Notice: Subject to any disclaimer, the term of this patent is extended or adjusted under 35 U.S.C. 154(b) by 52 days.

(21) Appl. No.: 13/133,140

(22) PCT Filed: Jan. 25, 2010

(86) PCT No.: PCT/NL2010/050033
§ 371 (c)(1),
(2), (4) Date: Sep. 20, 2011

(87) PCT Pub. No.: WO2010/085149
PCT Pub. Date: Jul. 29, 2010

(65) Prior Publication Data
US 2012/0029077 A1    Feb. 2, 2012

(30) Foreign Application Priority Data

Jan. 23, 2009  (EP) .................................... 09151285

(51) Int. Cl.
| | | |
|---|---|---|
| *A61K 31/23* | (2006.01) | |
| *A61P 31/04* | (2006.01) | |
| *C07C 53/126* | (2006.01) | |
| *A23K 50/80* | (2016.01) | |
| *A23K 20/158* | (2016.01) | |
| *A23K 50/70* | (2016.01) | |
| *A23K 50/75* | (2016.01) | |
| *A23K 50/30* | (2016.01) | |

(52) U.S. Cl.
CPC ............ *A23K 50/80* (2016.05); *A23K 20/158* (2016.05); *A23K 50/30* (2016.05); *A23K 50/70* (2016.05); *A23K 50/75* (2016.05); *A23V 2002/00* (2013.01)

(58) Field of Classification Search
CPC ...... A23K 1/1826; A23K 1/164; A23K 1/182; A23K 1/184; A23K 1/188; A23V 2002/00
See application file for complete search history.

(56) References Cited

U.S. PATENT DOCUMENTS

| | | | |
|---|---|---|---|
| 8,110,670 B2 * | 2/2012 | Hu et al. ...................... | 536/23.2 |
| 8,318,186 B2 * | 11/2012 | Msika et al. .................. | 424/401 |
| 2010/0239712 A1 * | 9/2010 | Brooks et al. ................. | 426/61 |
| 2011/0318434 A1 * | 12/2011 | Guthery ............... | A61K 9/0014 424/729 |

FOREIGN PATENT DOCUMENTS

| | | |
|---|---|---|
| WO | 2001052837 | 7/2001 |
| WO | 2001097799 | 12/2001 |
| WO | WO 2004/007416 A1 | 1/2004 |
| WO | 2006002927 | 1/2006 |
| WO | WO 2008062428 A2 * | 5/2008 ............. A01N 37/02 |

OTHER PUBLICATIONS

Kabara et al. 'Fatty Acids and Derivatives as Antimicrobial Agents' A Review In: Pharmacological Effects of Lipids, American Oil Chemist's Society, Jan. 1978, pp. 1-14.
Shibasaki et al. 'Combined Effects on Antibacterial Activity of Fatty Acids and Their Esters Against Gram-Negative Bacteria' Pharmacological Effects of Lipids, American Oil Chemist's Society, Jan. 1978, pp. 15-24.

* cited by examiner

*Primary Examiner* — Sarah Pihonak
*Assistant Examiner* — Jason A Deck
(74) *Attorney, Agent, or Firm* — Rudy J. Ng; Bret E. Field; Bozicevic, Field & Francis LLP

(57) ABSTRACT

The invention is directed to an animal feed suitable for feeding mammals, birds and fish, comprising an alkyl ester of a fatty acid, wherein said fatty acid has a chain length of 5-12 carbon atoms, and wherein the dosage of said ester in said animal feed is 50 ppm by weight or higher, based on the total weight of said animal feed.

23 Claims, 3 Drawing Sheets

Figure 2:
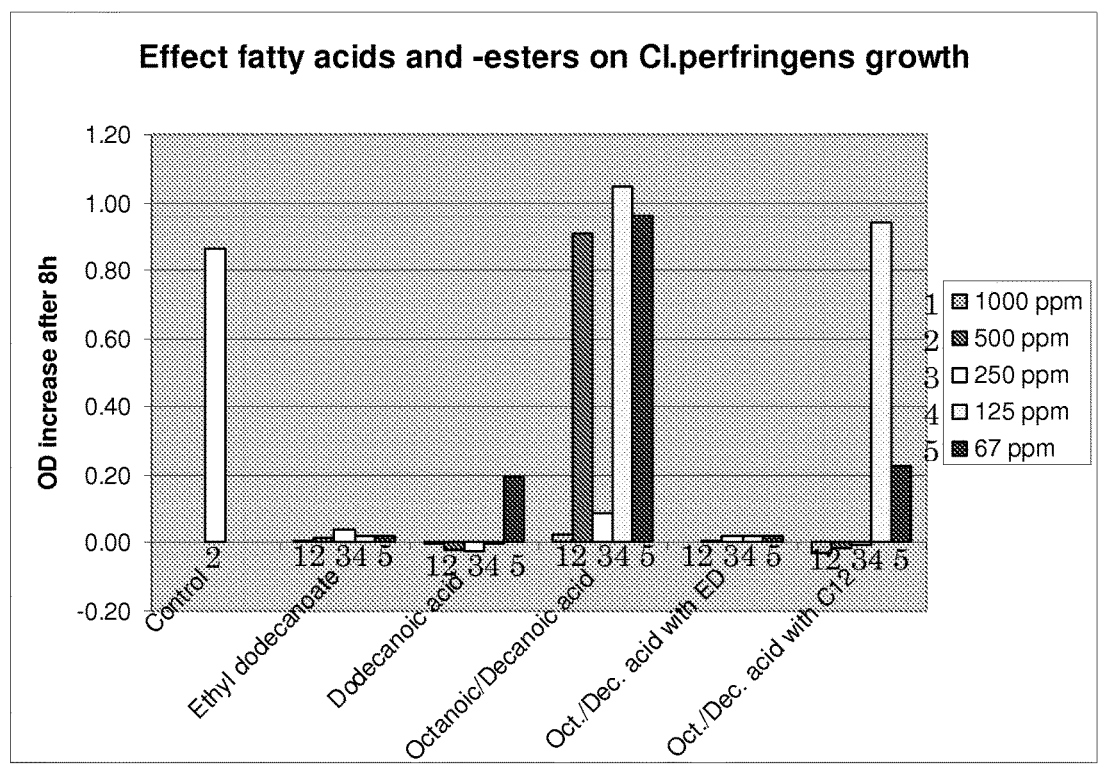

Figure 1.

ANIMAL FEED ADDITIVE AND ANIMAL FEED COMPRISING ALKYL ESTERS OF MEDIUM CHAIN FATTY ACIDS, AND THEIR USE IN ANIMAL FEED

The invention is directed to an animal feed and method for increasing feed efficiency and health in farming animals, including mammals, birds and fish.

The use of fatty acids as antimicrobial agents to inhibit growth of harmful microbes in living organisms has long been known in literature, see e.g. U.S. Pat. No. 2,466,663. A mixture of medium chain fatty acids (MCFAs) and organic acids is currently widely used to inhibit growth of pathogens in the gastrointestinal tract of animals. The presence of such a mixture in animal feed results in a favorable composition of the gastrointestinal microbiota and an improved feed efficiency in animals.

EP-A-1 059 041 discloses a feed supplement composition comprising at least one triglyceride containing MCFA and at least one exogenous lipolytic enzyme. The addition of this supplement to animal feed results in a physiological environment in the animal's gastrointestinal tract, including its stomach which regulates and stabilizes the gut microbiota and consequently results in improvement of growth in the animal.

WO-A-01/97799 discloses the use in feed compositions of one or more $C_6$-$C_{10}$ medium chain fatty acids, salts, derivatives or mixtures thereof for the inhibition of microbial contamination. However the specific use and effectiveness of alkyl esters of MCFAs as antimicrobial agents is not mentioned.

U.S. Pat. No. 4,526,798 discloses a mixture comprising the ethyl ester of 2-hydroxy-4-methyl-pentanoic acid, which mixture can be used in flavors that enhance the aroma or taste of tropical flavored foodstuffs. The concentration of the mixture in such flavors ranges from 0.75% to 1.2% by weight of the flavor. The resulting dosage of the ethyl ester in the foodstuff is low, for example 3-8 ppm. The effect of the mixture as an antimicrobial agent is not described in this document.

WO-2006/00297 discloses the use of MFCAs, derivatives thereof or mixtures for inhibiting the growth and/or for reducing the amount of microbial pathogens. This document also does not specifically mention alkyl esters of MCFAs and their effectiveness as an inhibitor of microbial pathogens.

WO-A-01/52837 discloses the use of a fatty ester for preparing a composition designed to inhibit 5-α-reducase activity in pharmacology, dermatology, cosmetics and as a food additive.

Karbara J. J., American Oil Chemist's Society, pp. 1-14, 1 Jan. 1978, discloses a review of fatty acids and derivatives as antimicrobial agents. However it does not specifically mention alkyl esters of MCFAs and their effectiveness as an antimicrobial agent.

Karbara J. J., American Oil Chemist's Society pp. 15-24, 1 Jan. 1978, discloses the combined effects on antibacterial activity of fatty acids and their esters with freezing or heating and the addition of chemicals such as citric acid against gram-negative bacteria. Further this review only discusses monoglycerides of MCFAs and not alkyl esters of MCFAs.

A disadvantage of the MCFAs and derivatives in animal feed of the prior art is that they are quickly absorbed in vivo in the proximal small intestinal tract. Consequently, they are not able to exert microbiota modulating properties in the distal small intestine and hind gut.

Other disadvantages of MCFAs are their corrosivity, their irritating odor and poor flavor. Ethyl esters and methyl esters are not corrosive, but esters based on the shorter chain MCFAs usually have a low flash point.

Another disadvantage is that in many cases MCFAs showed less pathogen activity than their ester counterparts because the esters possess non-specific activity of a surface-active agent (surfactant). Studies have demonstrated that the anti-bacterial, anti-fungal and anti-viral activities of the esters were due to their functions in disrupting cell membranes, see K. Nihei et al., J. Agric. Food Chem., 52 (2004)5011-5020.

Object of the present invention is to provide an animal feed that has strong antimicrobial and antipathogenic properties and results in a favorable composition of the gastrointestinal microbiota and improved feed efficiency in animals fed with said animal feed, and which overcomes at least in part one or more of the above-mentioned disadvantages of the prior art.

Figure 1:
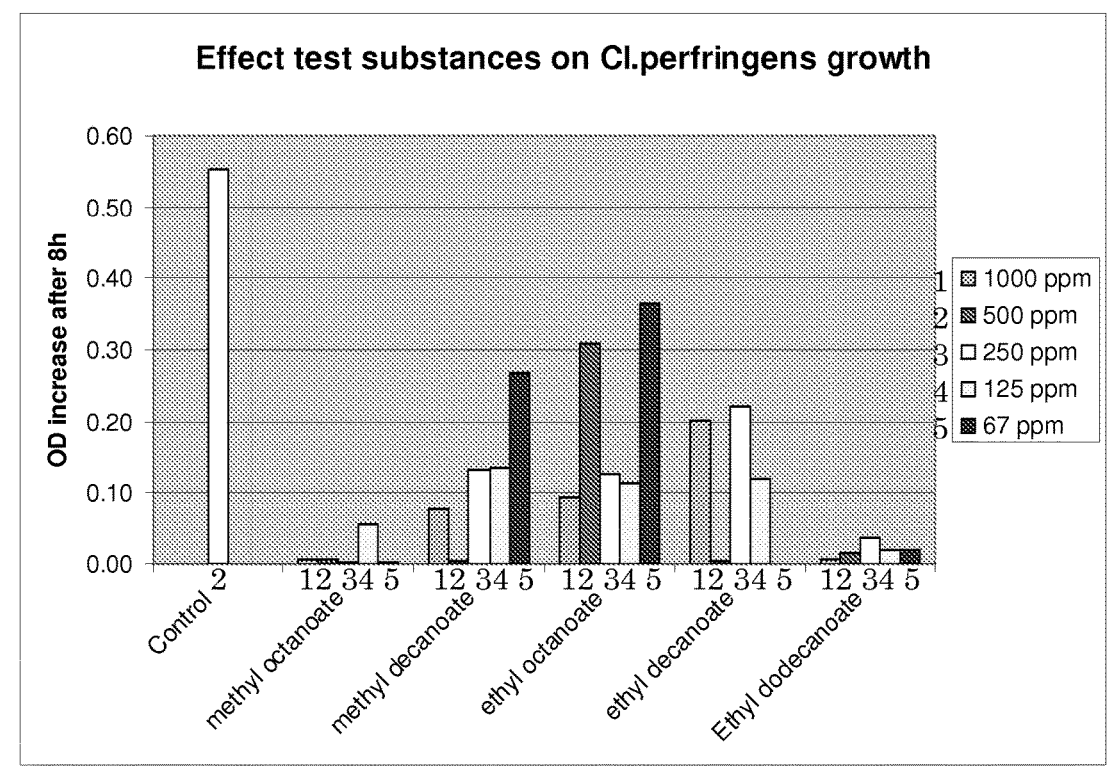

FIG. 1 shows the effect of different concentrations of methyl octanoate, methyl decanoate, ethyl octanoate, ethyl decanoate and ethyl dodecanoate on the growth of *Clostridium perfringens* in broth. The growth of *Clostridium perfringens* is measured over time (8 hours) by means of optical density (OD).

FIG. 2 shows the effect of different concentrations of ethyl dodecanoate, dodecanoic acid (C12), a blend of octanoic acid and decanoic acid, a combination of a blend of octanoic acid and decanoic acid with ethyl dodecanoate, and a combination of octanoic acid and decanoic acid with dodecanoic acid (C12). The growth of *Clostridium perfringens* is measured over time (8 hours) by means of optical density (OD).

Figure 3:
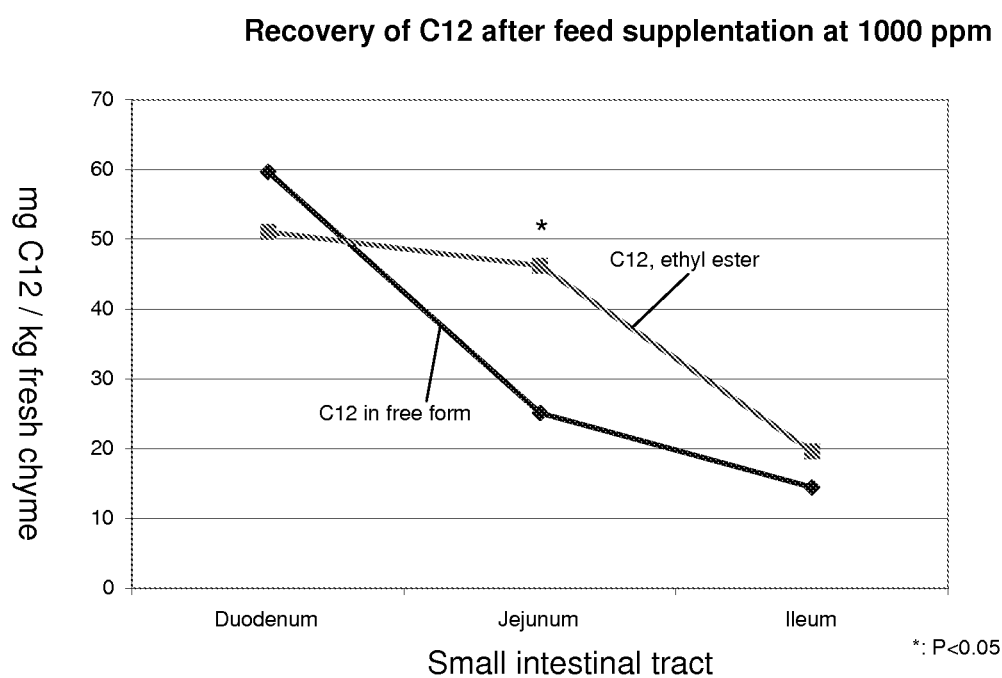

FIG. 3 shows the recovery of dodecanoic acid (C12) and the ethyl ester of dodecanoic acid (C12) in the duodenum, jejunum and ileum of broilers fed with 1000 ppm dodecanoic acid (C12) or the ethyl ester of dodecanoic acid (C12).

In a first aspect, this object is met by providing an animal feed suitable for feeding mammals, birds and fish, comprising an alkyl ester of a fatty acid, wherein said fatty acid has a chain length of 5-12 carbon atoms, and wherein the dosage of said ester in said animal feed is 50 ppm by weight or higher, based on the total weight of said animal feed.

In the present application, with a medium chain fatty acid (MCFA) is meant a fatty acid having a chain length of 5-12 carbon atoms, i.e. having a longest continuous chain of 5-12 carbon atoms. Preferably, the animal feed of the invention comprises an MCFA having a chain length of 8-12 carbon atoms. A chain length longer than 12 carbon atoms is not desirable, because this will have a negative influence on the degree of hydrolysis of the ester. In the present application, an MCFA having a chain length of x is sometimes referred to as $C_x$. For example, octanoic acid may be referred to as $C_8$.

The inventors found that the esters of MCFAs showed stronger anti-microbial activity than MCFAs and therefore provide stronger microbiota modulating properties inside the gut compared to MCFAs.

The inventors further surprisingly found that the esterified forms of MCFA according to the invention have a prolonged activity in the gastrointestinal tract compared to non-esterified forms of MCFA. In addition, it was found that alkyl esters of MCFAs according to the present invention are even more anti-microbial than their non-esterified counterparts. A further advantage of the animal feed of the present invention is that alkyl esters of MCFAs are still relatively cheap, although they are more expensive than plain MCFAs ($C_8$, $C_{10}$ and/or $C_{12}$).

The alkyl in the ester in the animal feed of the invention is preferably methyl, ethyl, propyl, butyl or a combination thereof.

The MCFA in the ester in the animal feed of the invention is preferably octanoic acid, decanoic acid, dodecanoic acid or a combination thereof.

The alkyl ester of MCFA in the animal feed of the invention is preferably methyl octanoate, methyl decanoate, methyl dodecanoate, ethyl octanoate, ethyl decanoate, ethyl dodecanoate, propyl octanoate, propyl decanoate, propyl dodecanoate, butyl octanoate, butyl decanoate, butyl dodecanoate or a combination thereof.

The dosage of the alkyl ester of MCFA in the animal feed of the invention is preferably 50 ppm by weight or higher, more preferably 100 ppm by weight or higher, most preferably 200 ppm by weight or higher, based on the total weight of the animal feed. A dosage lower than 50 ppm by weight may result in an insufficient antimicrobial effect. The dosage of the alkyl ester of MCFA in the animal feed of the invention should preferably be less than 5000 ppm by weight, preferably less than 1000 ppm by weight, more preferably less than 500 ppm by weight, based on the total weight of the animal feed. A disadvantage of using dosages higher than 5000 ppm by weight is that such dosages may have an undesired effect on the microbiotic balance. A further disadvantage of using high dosages is the resulting high cost price.

The gastrointestinal tract comprises the stomach, which has a pH of 3-4, the large intestine, which has a pH of 6-7, and the small intestine, which has a pH of about 7. Microorganisms, both pathogens and neutral or beneficial microorganisms, are in particularly present in the large and the small intestine.

Without wishing to be bound by theory, it is believed that the absorption of MCFAs is delayed by the esterified form according to the present invention. In this way the bioactive form of alkyl esters of MCFA will be able to express its bioactivity as far as the distal small intestinal tract, e.g. the distal end of the small intestines, which is crucial for modulating the local microbiota, resulting in improved efficiency of nutrient utilization (feed efficiency). The feed conversion ratio (FCR) is a measure of an animal's efficiency in converting feed mass into increased body mass and can be defined as the mass of the food eaten divided by the body mass gain, all over a specified period of time. The ability of alkyl esters of MCFA to express its bioactivity in the small intestine may also be beneficial for the control of important potential enteric pathogens that are mainly situated in the distal intestinal tract. Examples of such pathogens are *Clostridium perfringens, Streptococcus suis, Escherichia coli* and *Salmonella* spp.

Microorganisms can be divided into gram-negative and gram-positive microorganisms. An example of gram-negative microorganisms is *Escherichia coli*, which is the causative agent of diarrhea in pigs. An example of a gram-positive microorganism is *Clostridium perfringens*, which microorganism plays an important role in development of *Necrotic Enteritis* in the small intestine of broiler chickens.

The balance in the gastrointestinal tract is very important for prevention and treatment of enteric infections in living organism. For example, it is important for the health of a living organism that each part of the gastrointestinal tract has a certain pH range and that there is a favorable composition of different microorganisms present in each part of the gastrointestinal tract. The balance in the gastrointestinal tract may be influenced by adding additives to the animal feed.

Alkyl esters of MCFA have no significant effect on the pH in the intestines. Alkyl esters of MCFA act on the membrane of microorganisms of both pathogens and neutral and beneficial microorganisms, thus disabling and/or destroying the microorganisms.

The animal feed according to the present invention works in two ways. In the first place, pathogens are inhibited by the antimicrobial property of the alkyl esters of MCFA, thereby decreasing the risk of infections. Furthermore, the decrease in microbial activity of microorganisms in general in the gastrointestinal tract results in a decrease in the feed conversion ratio (FCR), corresponding to an improved feed efficiency in the animal.

It was found that alkyl esters of MCFA are particularly suitable for inhibition of gram-positive bacteria, while organic acids are particularly suitable for inhibition of gram-negative bacteria. The mode of action on microbes of MCFA and organic acids differs. It was further found that the combination of alkyl esters of MCFA and organic acids may have a synergistic effect on the inhibition of harmful microbes and on lowering the microbial activity in general. Alkyl esters of MCFA, in particular ethyl esters of MCFA, disrupt the barrier properties of the membrane of the microbe, thereby enhancing the passage of organic acids into the microbial cell, which leads to inhibition of essential metabolic pathways. Therefore, it may be preferable to add one or more organic acids to the animal feed according to the present invention. Examples of preferable organic acids are one or more of valeric acid (pentanoic acid), caprylic acid (octanoic acid), capric acid (decanoic acid), formic acid, acetic acid, propionic acid, lactic acid, butyric acid, citric acid, malic acid, fumaric acid, benzoic acid, succinic acid, sorbic acid, tartaric acid, or sodium-, potassium-, ammonium-, or calcium salts thereof.

Additionally, gallic acid or an alkyl ester of gallic acid may be added to the animal feed according to the invention. Gallic acid and alkyl ester of gallic acid also have antimicrobial properties. It was found that animal feed comprising an alkyl ester of MCFA in combination with gallic acid and/or an alkyl ester of gallic acid has a synergistic effect on the antimicrobial properties of these molecules in the gastrointestinal tract, thereby significantly improving the bioactivity of these molecules. Examples of particularly preferred alkyl esters of gallic acid that may be added to the animal feed of the invention are propylgallate, pentyl gallate, octyl gallate, and lauryl gallate.

The animal feed according to the invention is suitable for all animals, including mammals, fish and birds. It is particularly suitable for animals having a single stomach, for example for pigs or poultry.

The invention is furthermore directed to an ingredient, premix or supplement for an animal feed suitable for feeding mammals, birds and fish, comprising an alkyl ester of a fatty acid, wherein said fatty acid has a chain length of 5-12 carbon atoms, and wherein the dosage of said ester in said animal feed is 1 wt. % or higher. Such an ingredient, premix or supplement may further comprise one or more of the following additives: micro ingredients, such as vitamins and trace elements; MCFA; minerals and organic acids.

The invention is further directed to a method for increasing the feed efficiency and/or decreasing the risk of infections in animals comprising feeding a mammal, bird or fish with the animal feed, ingredient, premix or supplement of the present invention.

The invention is also directed to the use of an alkyl ester of MCFA or an alkyl ester of MCFA enriched product in the preparation of a feed supplement for the improvement of feed efficiency and/or decreasing the risk of infections in an animal.

The invention is now elucidated on the basis of some examples, which are not intended to limit the scope of the invention.

EXAMPLES

Example 1

Inhibition of *Clostridium perfringens* by Various Methyl and Ethyl Esters of Medium Chain Fatty Acids A spectrophotometer was used to measure growth of micro organisms in broth over time (8 hours) by means of optical density (OD) for broths inoculated with specific bacterial strains. The relative decrease of OD is a measure of inhibitory strength. Broths were treated with graded levels of potential inhibitory substances and incubated for 24 hours.

Treatments used were the following methyl octanoate; ethyl octanoate; methyl decanoate; ethyl decanoate; ethyl dodecanoate.

The results are given in FIG. 1. From FIG. 1 it can be seen that ethyl dodecanoate shows complete inhibition at all tested levels, while methyl octanoate shows nearly the same results. It can be concluded that from all the treatments used ethyl dodecanoate is the most effective inhibitor against *Clostridium perfringens*.

Example 2

Inhibition of *Clostridium perfringens* by Lauric Acid (C12) and its Ethyl Ester (EL) Either or not in Combination with Octanoic/Decanoic Acid (C8/C10)

A spectrophotometer was used to measure growth of micro organisms in broth over time (8 hours) by means of optical density of broths inoculated with specific bacterial strains. The relative decrease of OD is a measure of inhibitory strength. Broths are treated with graded levels of potential inhibitory substances and incubated for 24 hours.

Treatments used were the following: ethyl dodecanoate (ED); dodecanoic acid (C12); blend of octanoic/decanoic acid (C8/C10); combination of C8/C10 and ED (50/50); combination of C8/C10 and C12 (50/50).

The results are given in FIG. 2. From FIG. 2 it can be seen that ethyl ester of dodecanoic acid demonstrated complete inhibition of *Clostridium perfringens* even at the lowest inclusion level of treatment whereas dodecanoic acid was not as effective as effective at 67 ppm. The combination of octanoic/decanoic acid and ethyl dodecanoate also was effective in inhibiting *Clostridium perfringens* at all levels of treatment.

Therefore it can be concluded that the ethyl ester has a higher inhibitory strength than the free fatty acid, but a comparable inhibitory effect to that of the combination of octanoic/decanoic acid and ethyl dodecanoate.

Example 3

Effect of 1000 ppm of Ethyl Dodecanoate or Dodecanoic Acid in the Feed of Broilers on Recovery in the Various Segments of the Gastro Intestinal Tract Broilers were offered feed supplemented with 1000 ppm of either dodecanoic acid or ethyl dodecanoate throughout the trial. At day 43 of age, 12 birds per treatment were sacrificed and the content of the duodenum, jejunum and ileum was harvested and analysed for levels of ethyl dodecanoate and dodecanoic acid. In FIG. 3 the mean levels are depicted.

FIG. 3 shows that the level of the ethyl ester is higher than the free fatty acid in the jejunum. Therefore it can be concluded that the ethyl ester is not as quickly adsorbed through the intestinal wall as the free fatty acid.

Example 4

Effect of 1000 ppm of Ethyl Dodecanoate or Dodecanoic Acid in the Feed of Broilers, Inoculated with *Clostridium*, on Subsequent *Clostridium* Counts in Jejunum Broilers were housed in group pens and offered feed supplemented with 1000 ppm of ethyl dodecanoate or dodecanoic acid. Parallel trials were conducted, one with normal birds and one with birds which were inoculated with $10^8$ CFU *Clostridium perfringens* at day 9 through 11 birds. At day 13 of age, *Clostridium* counts were measured in fresh chime taken in the jejunum (see table 1). It was found that the feed supplemented by ethyl ester of dodecanoic acid led to an overall significant reduction of *Clostridium* counts. The effect was largest when the broilers were stressed by *Clostridium* inoculation.

TABLE 1

*Clostridium perfringens* counts in jejunum of infected and normal broilers on day 13 of age.

| Animal model | Supplementation in feed | | |
|---|---|---|---|
| | C12 free form | C12 ethyl ester | P-level |
| Non-challenged | 1.418 | 1.048 | p = 0.15 |
| Challenged | 2.122 | 0.977 | p = 0.24 |
| Overall | 1.770 | 1.013 | p = 0.08 |

These results demonstrate that supplementation with ethyl dodecanoate provides a stronger inhibition of *Clostridium perfringens* in jejunum than supplementation with equal levels of dodecanoic acid. This effect can most probably be attributed to the higher residual levels of degradation product of ethyl dodecanoate (viz. dodecanoic acid) in the jejunum (see example 3, FIG. 3).

Example 5

Effect of 1000 ppm of Ethyl Dodecanoate or Dodecanoic Acid in the Feed of Broilers, Inoculated with *Clostridium*, on Growth, Feed Conversion and Mortality In broilers infected at day 9-11 with *Clostridium perfringens*, weight gain, feed conversion ratio and mortality was followed for 6 weeks (42 days). The feed was either supplemented with ethyl dodecanoate or with dodecanoic acid at 1000 ppm. An overall improvement was shown for all the parameters measured in the group of ethyl dodecanoate (table 2) as compared to the free fatty acid.

TABLE 2

Growth, feed conversion and mortality of *Clostridium perfringens* infected broilers

| 0-42 day performance | 1000 ppm Dodecanoic acid | 1000 ppm Ethyl dodecanoate |
|---|---|---|
| Weight gain, g/day | 63.78 | 65.5 |
| Feed intake, g/day | 104.3 | 106.5 |
| Feed conversion ratio | 1.636 | 1.626 |
| Mortality, % | 8.333 | 4.621 |

From table 2 it can be concluded that the ethyl ester of dodecanoic acid results in a better zootechnical performance than dodecanoic acid itself.

Example 6

Effect of 1000 ppm of Ethyl Dodecanoate or Dodecanoic Acid in the Feed of Piglets on Zootechnical Performance and Diarrhoea A trial was conducted wherein the effect of 1000 ppm of dodecanoic acid or 1000 ppm ethyl dodecanoate on the feed of 108 weaned piglets housed in group pens (n=9 per treatment), was tested. The effect on average diarrhoea score (over the total period) per treatment is shown below in table 3:

TABLE 3

Diarrhoea score of weaned piglets fed with ethyl dodecanoate or dodecanoic acid supplements

| | Treatment | | Overall | | | |
|---|---|---|---|---|---|---|
| Days | Control | Ethyl-C12 | C12 | mean | std | $\chi^2$ | p-value[1] |
| Diarrhoea score | 49.84 a | 46.64 ab | 42.41 b | 48.01 | 20.75 | 7.55 | 0.056 |

From table 3, it can be seen that ethyl dodecanoate was able to significantly reduce diarrhoea whereas dodecanoic acid did not. Therefore it can be concluded that the effect on pathogenic bacteria in the intestinal tract of piglets of ethyl ester is stronger than of the related fatty acid.

Example 7

Effect of Blend of Medium Chain Fatty Acids and Ethyl Dodecanoate in Piglet

In a trial with 48 individually housed piglets the effect of a blend of medium chain fatty acids (octanoic, decanoic, dodecanoic acid) and ethyl dodecanoate in the relative proportion 30%:37%:18%:15% was tested. This blend was dosed at a total level of 1000 ppm in the weaner feed and was offered in the first 4 weeks after weaning. The piglets were infected with β-hemolytic *E. coli* (O149:K88acK91) at day 6 after weaning. At day 21 after weaning faeces samples were collected from 8 piglets per treatment and microbiological counts were measured. Further, each piglet was visually scored for faecal consistency in the same period (20-27 days after weaning) to determine the diarrhoea score.

TABLE 4

Microbiological counts of faeces and diarrhoea score of piglets infected with β-hemolytic *E. coli*

| | Enterobacteria | *E. coli* | *Lactobacillus* | Diarrhoea score |
|---|---|---|---|---|
| 1. Control | 6.7740 a | 6.2431 a | 7.7108 | 38.1% |
| 2. MCFA and esters | 5.4452 b | 5.2044 b | 7.9165 | 25.0% |
| Standard deviation | 1.4179 | 1.2158 | 0.8964 | n.a. |
| p value | p < 0.10 | p < 0.10 | p > 0.10 | p > 0.10 |

From table 4 it can be seen that a blend of medium chain fatty acids and esters can reduce microbial contamination by pathogenic species like *E. coli* (part of the family of Enterobacteria) and indeed reduce the number of cases of diarrhoea. Moreover, commensal microbial species like *Lactobacillus* were not inhibited.

The invention claimed is:

1. An animal feed suitable for feeding mammals, birds and fish, comprising an alkyl ester of a fatty acid in an amount effective to inhibit gastrointestinal microbial pathogens, wherein said fatty acid has a chain length of 5-12 carbon atoms, and wherein the dosage of said ester in said animal feed is 50 ppm by weight or higher, based on the total weight of said animal feed.

2. The animal feed according to claim 1, wherein said alkyl is methyl, ethyl, propyl, butyl or a combination thereof.

3. The animal feed according to claim 1, wherein said fatty acid has a chain length of 8-12 carbon atoms.

4. The animal feed according to claim 1, wherein said fatty acid is octanoic acid, decanoic acid, dodecanoic acid or a combination thereof.

5. The animal feed according to claim 1, wherein said ester is methyl octanoate, methyl decanoate, methyl dodecanoate, ethyl octanoate, ethyl decanoate, ethyl dodecanoate, propyl octanoate, propyl decanoate, propyl dodecanoate, butyl octanoate, butyl decanoate, butyl dodecanoate or a combination thereof.

6. The animal feed according to claim 1, wherein the dosage of said ester in said animal feed is 100 ppm by weight or higher, based on the total weight of said animal feed.

7. The animal feed according to claim 1, wherein the dosage of said ester in said animal feed is less than 5000 ppm by weight, based on the total weight of said animal feed.

8. The animal feed according to claim 1, further comprising organic acids and/or salts thereof.

9. The animal feed according to claim 8, wherein said organic acid and/or said salt thereof is chosen from the group consisting of pentanoic, octanoic, decanoic, formic, acetic, propionic, lactic, butyric, citric, malic, fumaric, benzoic, succinic, sorbic, tartaric acid and/or salt and combinations thereof.

10. The animal feed according to claim 1, further comprising gallic acid or an alkyl ester of gallic acid.

11. The animal feed according to claim 10, wherein said alkyl ester of gallic acid is propyl gallate, pentyl gallate, octyl gallate or lauryl gallate.

12. An ingredient, premix or supplement for an animal feed suitable for feeding mammals, birds and fish, comprising an alkyl ester of a fatty acid in an amount effective to inhibit gastrointestinal microbial pathogens, wherein said fatty acid has a chain length of 5-12 carbon atoms, and wherein the dosage of said ester is 1 wt. % or higher based on the total weight of said ingredient, premix or supplement, wherein said ingredient, premix or supplement further comprises vitamins, trace elements, minerals and organic acids.

13. A method for increasing the feed efficiency and/or decreasing the risk of infections in an animal in farming comprising feeding a mammal, bird or fish with the animal feed according to claim 1.

14. A method of preparing an animal feed according to claim 1 for the improvement of feed efficiency and/or decreasing the risk of infections in an animal, comprising including an alkyl ester of claim 1 or an alkyl ester enriched product comprising an alkyl ester of claim 1 in the animal feed, in an amount effective to inhibit gastrointestinal microbial pathogens.

15. The animal feed according to claim 6, wherein the dosage of said ester in said animal feed is 200 ppm by weight or higher, based on the total weight of said animal feed.

16. The animal feed according to claim 15, wherein the dosage of said ester in said animal feed is less than 1000 ppm by weight, based on the total weight of said animal feed.

17. The animal feed according to claim 1, wherein the dosage of said ester in said animal feed is 200 ppm by weight or higher, based on the total weight of said animal feed.

18. The animal feed according to claim 1, wherein the dosage of said ester in said animal feed is less than 1000 ppm by weight, based on the total weight of said animal feed.

19. The animal feed according to claim 2, wherein the dosage of said ester in said animal feed is 1000 ppm or less by weight, based on the total weight of said animal feed.

20. The animal feed according to claim 5, wherein the dosage of said ester in said animal feed is 1000 ppm or less by weight, based on the total weight of said animal feed.

21. The animal feed according to claim 1, wherein the dosage of said ester in said animal feed is 50 ppm to 100 ppm by weight, based on the total weight of said animal feed.

22. An animal feed suitable for feeding a mammal, bird or fish, comprising ethyl dodecanoate in an amount effective to inhibit *Clostridium perfringens* in a small intestine of said mammal, bird or fish, wherein said ethyl dodecanoate is present in said animal feed in a dosage of 50 ppm by weight or higher, based on the total weight of said animal feed.

23. A method for increasing the feed efficiency and/or decreasing the risk of infections in an animal in farming comprising feeding a mammal, bird or fish with the ingredient, premix or supplement according to claim 12.

* * * * *